(12) United States Patent
Izquierdo

(10) Patent No.: US 12,318,085 B2
(45) Date of Patent: Jun. 3, 2025

(54) SELF-KNOTTING SUTURE DEVICE

(71) Applicant: Luis Izquierdo, Lawrenceville, GA (US)

(72) Inventor: Luis Izquierdo, Lawrenceville, GA (US)

( * ) Notice: Subject to any disclaimer, the term of this patent is extended or adjusted under 35 U.S.C. 154(b) by 344 days.

(21) Appl. No.: 18/105,078

(22) Filed: Feb. 2, 2023

(65) Prior Publication Data

US 2023/0240675 A1    Aug. 3, 2023

Related U.S. Application Data

(60) Provisional application No. 63/305,760, filed on Feb. 2, 2022.

(51) Int. Cl.
*A61B 17/04* (2006.01)
*A61B 17/00* (2006.01)

(52) U.S. Cl.
CPC ...... *A61B 17/0469* (2013.01); *A61B 17/0467* (2013.01); *A61B 17/0482* (2013.01); *A61B 17/0485* (2013.01); *A61B 2017/00199* (2013.01); *A61B 2017/047* (2013.01)

(58) Field of Classification Search
CPC ............ A61B 17/0469; A61B 17/0467; A61B 17/0482; A61B 17/0485; A61B 2017/0496; A61B 17/0483
See application file for complete search history.

(56) References Cited

U.S. PATENT DOCUMENTS 8,568,445 B2 * 10/2013 Pipenhagen ....... A61B 17/0057
606/213

* cited by examiner

*Primary Examiner* — Julian W Woo
(74) *Attorney, Agent, or Firm* — Michael D. Meyer; Jerome D. Drabiak; EDISON LAW GROUP

(57) ABSTRACT

A self-knotting suture device includes a base configured for contact with a living tissue, and the base includes an opening for passage of a suture material. A knotting mechanism includes a finger configured to receive an end of the suture material, and a grabber arranged substantially transverse to the suture material in a path to the finger. The grabber is configured to rotate so as to twist the suture material into one or more intertwined loops. A tensioner is configured to adjust a tension of the suture material to form a knot of the intertwined loops when tension is increased. A blade mechanism is configured to cut the suture material adjacent the finger.

21 Claims, 4 Drawing Sheets

SELF-KNOTTING SUTURE DEVICE

BACKGROUND

Technical Field

The present disclosure generally relates to medical devices used to hold body tissues together, and more particularly to sutures.

Description of the Related Art

Sutures are used to sew stitches that close a cut or an opening in a living body. For example, a surgical suture may include a needle with a piece of thread that is a certain length. A surgical knot is used to bind the suture material (e.g., surgical thread) together so that the stitches do not unravel and permit a safe and effective healing of a cut. Whether the cut in the skin as made by a surgeon, or occurred because of an accident, the stitches serve the same purpose.

Suture material may be either absorbable or nonabsorbable. The use of nonabsorbable suture material sometimes results in a patient having to return to a surgeon's office to remove the sutures after the opening has nearly healed.

Regardless of the type of suture material being used, the proper tying of a surgical knot is a surgical skill that is a part of many medical disciplines. However there are many different types of suture materials. Some suture material is braided, which makes tying a surgical knot a challenging skill. When such knots are tied internally, including but not limited to a laparoscopic and/or a robotic procedures procedure, there can be increased difficulty in performing this skill. In addition, the suture string is typically cut after the knot is tied. The knotting and suturing are often performed with equipment such as pliers (e.g. needle node pliers) and scissors. Such equipment must be properly sterilized before each use, and extreme care has to be exercised so as not to damage a patient's tissue, and/or to damage the stitches.

SUMMARY

In one embodiment, a self-knotting suture device includes a base configured for contact with a living tissue, and the base includes an opening for passage of a suture material. A knotting mechanism includes a finger configured to receive an end of the suture material, and a grabber arranged substantially transverse to the suture material in a path to the finger. The grabber is configured to rotate to twist the suture material into one or more intertwined loops. A tensioner is configured to adjust a tension of the suture material to form a knot of the intertwined loops when tension is increased. A blade mechanism is configured to cut the suture material adjacent the finger.

In an embodiment, a needle assembly is configured to receive the suture material and pierce the living tissue, and a slide trigger configured to be slid from a first position to a second position to extend move the needle to form a stitch in the living tissue with the suture material.

In an embodiment, the slide trigger is further configured to be slid to a third position to actuate the knotting mechanism and tie a knot in the suture material.

In an embodiment, the slide trigger manually moves the needle and actuates the knotting mechanism based on a position of the slide trigger.

In an embodiment, a motor is arranged to move the needle and actuate the knotting mechanism based on a position of the slide trigger.

In an embodiment, the slide trigger is further configured to be slid to a fourth position to cut the knotted suture material.

In an embodiment, the slide trigger further includes buttons connected to a motor to move the needle, and to actuate the knotting mechanism.

In an embodiment, the slide trigger actuates the blade mechanism to cut the suture material when the slide trigger is moved to a cutting position.

In an embodiment, the grabber is a hook, and the knotting mechanism includes a gear and shaft assembly for rotating the hook.

In an embodiment, the blade mechanism is a knife, and an actuator is connected to the knife.

In an embodiment the actuator includes a spring.

In an embodiment, a housing is included in which the knotting mechanism and the blade mechanism are arranged.

In an embodiment, a handle is attached to the housing.

In an embodiment, grips attached to an exterior of the handle.

In an embodiment, a camera is arranged in the base, and a wireless transmitter is configured to transmit images received by the camera.

In an embodiment, a display is arranged in a surface of the housing that displays images received by the camera.

In one embodiment, a self-knotting suture device includes a base configured for contact with a living tissue, wherein the base includes an opening for passage of a suture material. A tensioner is configured to adjust a tension of the suture material. The suture device includes a knotting means for twisting the suture material into one or more intertwined loops to form a knot of the intertwined loops. A blade mechanism is configured to cut the suture material extending from the knot.

In an embodiment, the base is configured for contact with internal living tissue, and the suture device further includes a camera arranged in the base, and a wireless transmitter configured to transmit the images from the camera.

In an embodiment, the knotting means is mechanically actuated.

In an embodiment, the knotting means is electrically actuated.

In an embodiment, the knotting means is actuated via a slide trigger.

These and other features will become apparent from the following detailed description of illustrative embodiments thereof, which is to be read in connection with the accompanying drawings.

BRIEF DESCRIPTION OF THE DRAWINGS

The drawings are of illustrative embodiments. They do not illustrate all embodiments. Other embodiments may be used in addition to or instead. Details that may be apparent or unnecessary may be omitted to save space or for more effective illustration. Some embodiments may be practiced with additional components or steps and/or without all the components or operations that are illustrated. When the same numeral appears in different drawings, it refers to the same or like components or operations.

DETAILED DESCRIPTION

Overview

In the following detailed description, numerous specific details are set forth by way of examples to provide a thorough understanding of the relevant teachings. However, it should be understood that the present teachings may be practiced without such details. In other instances, well-known methods, procedures, components, and/or circuitry have been described at a relatively high level, without detail, to avoid unnecessarily obscuring aspects of the present teachings.

Example Embodiments

Figure 1:
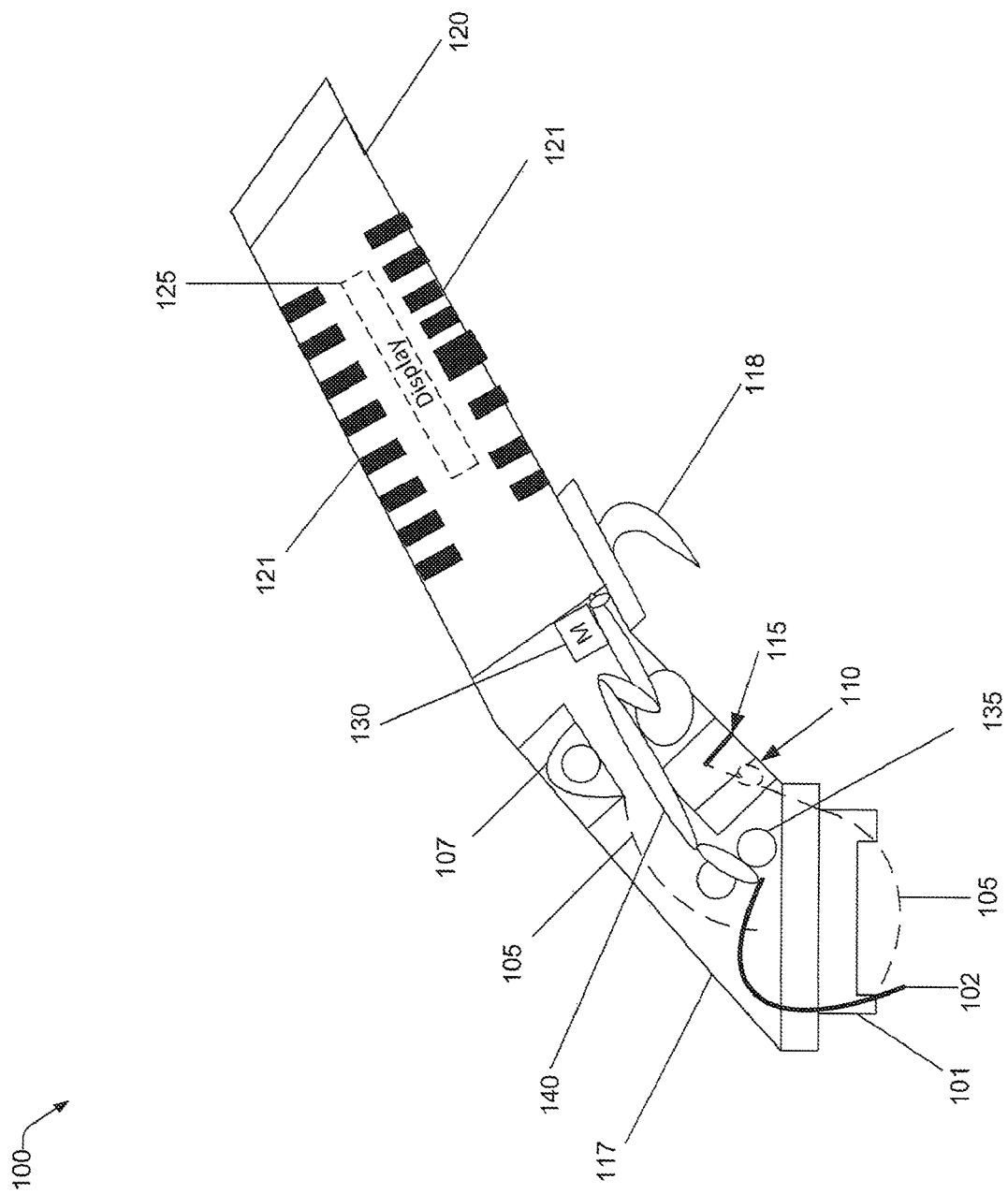
FIG. 1 is an overview of a self-knotting suture device according to an embodiment of the present disclosure.

FIG. 1 is an overview of a self-knotting suture device 100 according to an embodiment of the present disclosure. The suture device 100 includes a base 101 that has an opening for a needle 102 threaded with a suture material 105, The needle 102 can extend and retract to make a stitch in the living tissue. In a non-limiting example, the base is configured for contact with the living tissue (e.g., skin, or an internal tissue) as the suture device makes one of more stitches. However, the base may not contact the living tissue, and hover over the tissue being stitched.

The suture material 105, which may be any kind of material suitable for stitching living tissue, including braided suture material, may be used. The suture material 105 may also be a "dissolvable" type that essentially dissolves into the body over a period of time without requiring removal, or a non-dissolving type, that typically requires removal by a qualified health practitioner after a recommended period of time. A spool 107 may have the suture material 105 wrapped thereon, and through the movement of the needle 102 by the operation of gears 135, pivoting rods 140, and possible a motor 130. The direction of the rotation of the gears 135 may also cause a movement of the pivoting rods 140. The suture material is pulled off the spool 107 and used to stitch closed an opening that exists in a living tissue. The opening, for example, may be caused by an injury, or made by a surgeon's cut.

The suture device 100 includes a knotting mechanism 110 and a cutting blade 115. The knotting mechanism 110 is shown in more detail in FIGS. 2 and 3. The knotting mechanism 110 operates to self-knot the suture material. In other words, instead of having a surgeon/healthcare practitioner carefully create a loop with the suture material using pliers, and threading the loop with the suture material to form a knot, the knotting mechanism performs this tasks.

In an illustrative embodiment, the cutting blade includes a biasing, such as a spring, is arranged so that the blade 115 will cut the suture material 105 to remove a string extending from the knot. The blade 115 may also be pivotable and/or retractable to facilitate cutting the suture material 105 as close to the knot as possible. A housing 117 can be attached to, or extend from, the base 101, and many of the items shown in FIG. 1 are arranged within the housing 117.

The trigger 118 may be slidable to various positions. The suture device 100 may be mechanically operated, or electromechanically operated, and the trigger 118 is configured for the aforementioned types of operations. For example, the trigger 118 can be slidable to different positions along the suture device 100. Some of the positions will cause the position of the pivoting rods 140 to change, and extend (e.g., move) a position of the needle 102. For example, when the slide trigger 118 is configured to be slid from a first position to a second position to move a position of the needle 102 to form a stitch in the living tissue with the suture material. In addition, when the slide trigger is slidable to a third position to actuate the knotting mechanism to tie a knot in the suture material. The slide trigger 118 can be further configured to be slid to a fourth position to cut the knotted suture material. It is to be understood that the order and number of functions performed by changing the position of the trigger can be different than those described herein. Also, the term "slidable" should be interpreted broadly, and pulling the trigger a certain number of times to select a certain function is one of many ways to practice the teachings of the present disclosure.

The suture device may include a handle 120 with grips 121. An optional display 125 may be arranged in a surface of the handle 120. It is to be understood the display may be arranged elsewhere in the suture device 100 than shown in FIG. 1, which is provided only for illustrative purposes.

Figure 2:
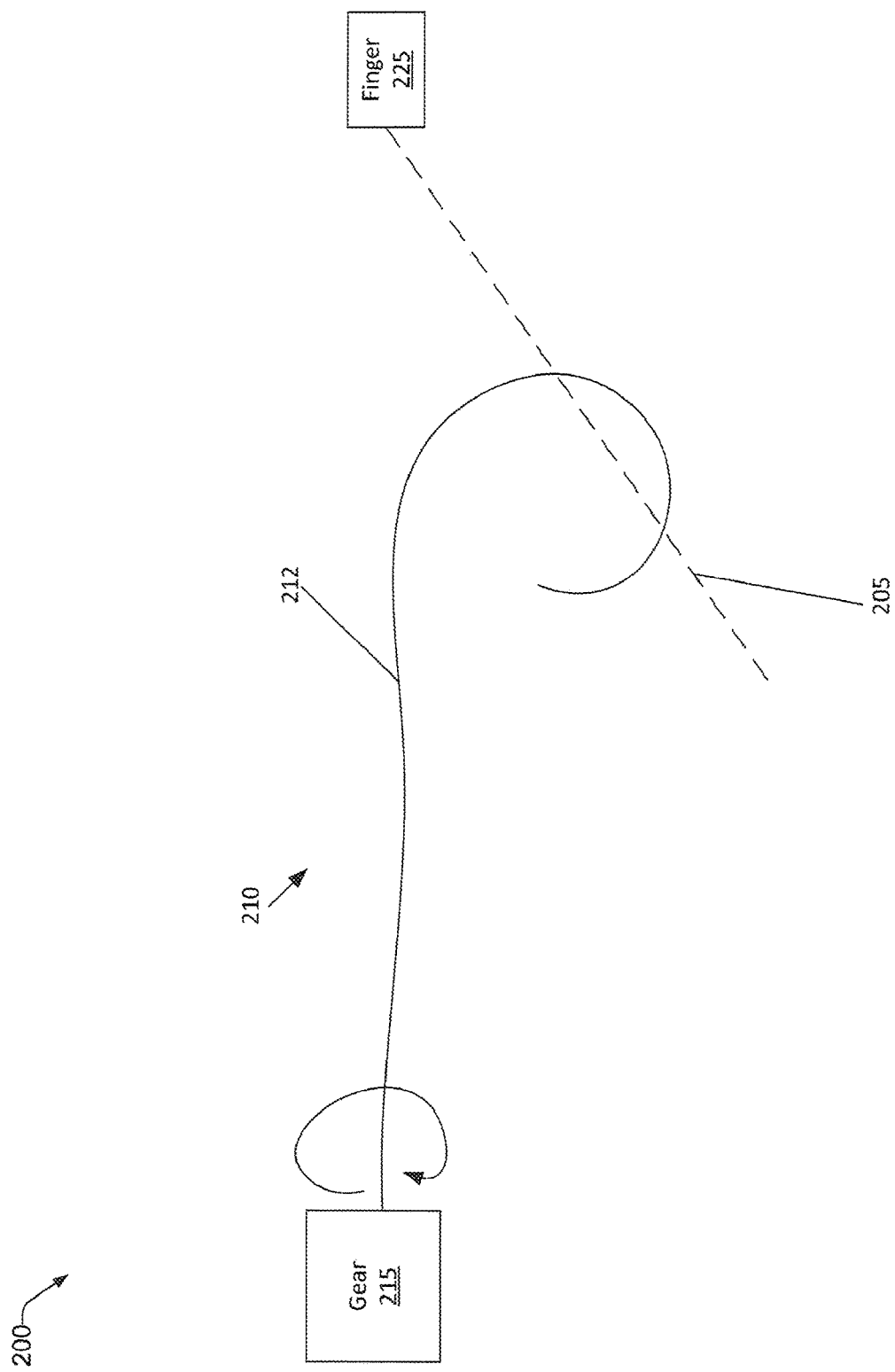
FIG. 2 illustrates a portion of the knotting mechanism of the self-knotting suture device according to an embodiment of the present disclosure.

FIG. 2 illustrates a portion 200 of the knotting mechanism 210 of the self-knotting suture device according to an embodiment of the present disclosure. The knotting mechanism 210 includes a grabber 212. While the grabber 212 shown in FIG. 2 (and grabber 312 in FIG. 3), as hook, it is to be understood that any type of shape that is preferably not strictly linear (e.g., wavy, curved, etc., that is arranged substantially transverse to the position of the suture material may be employed. The grabber 212 is attached to a gear 215 and shaft assembly. FIG. 2 shows one direction (e.g. clockwise) the gear and shaft assembly 215 may rotate the grabber 212. However, the rotation may also be counterclockwise. The suture material 15 typically passes over the grabber 212, but it could pass underneath, as the rotation of the grabber 212 will cause loops to form to create a knot. The finger 225 receives the other end of the suture material 205.

Figure 3:
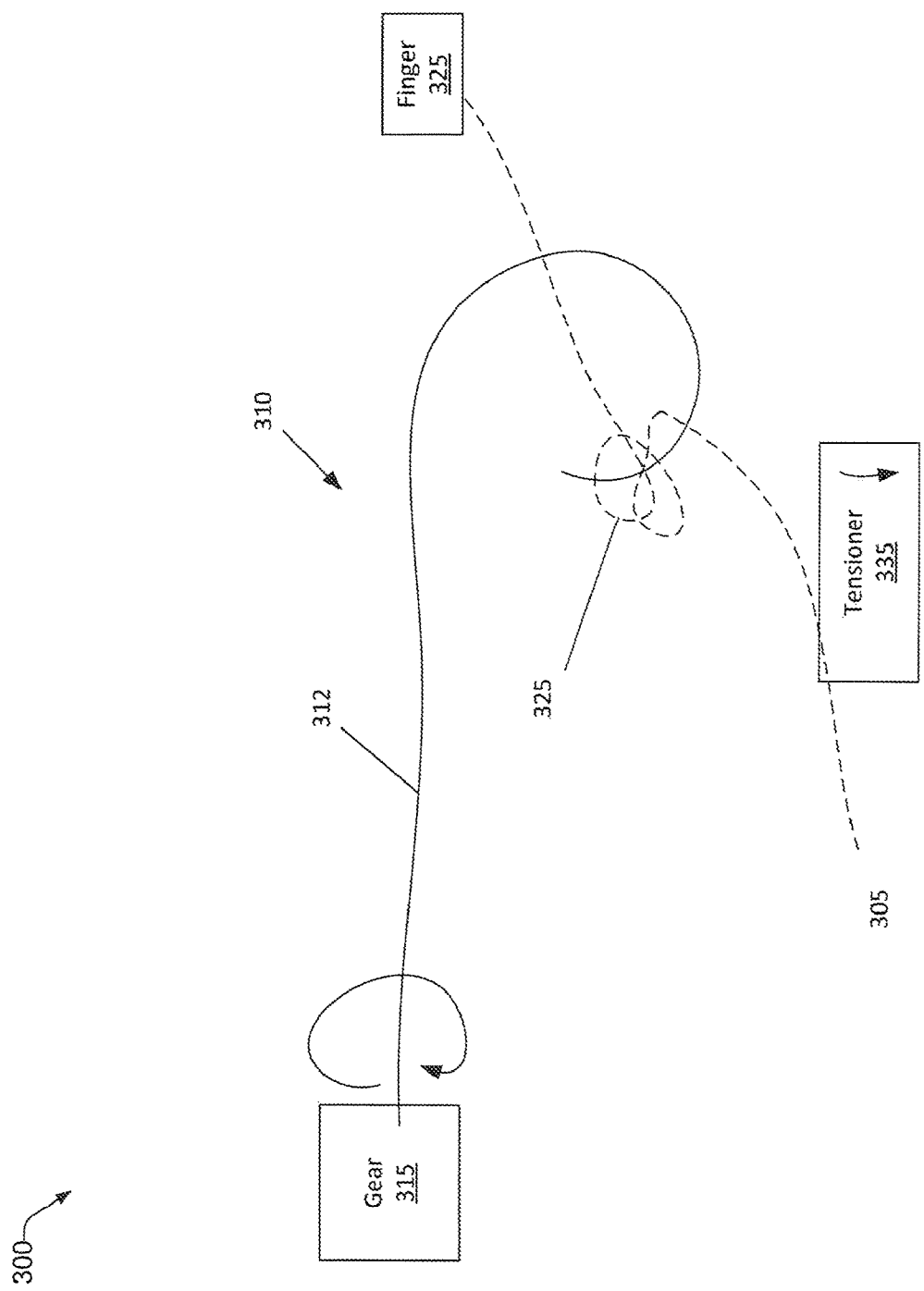
FIG. 3 illustrates a portion of the self-knotting mechanism making loops to tie a knot according to an embodiment of the present disclosure.

FIG. 3 illustrates a portion of the self-knotting mechanism making loops to tie a knot according to an embodiment of the present disclosure. Presuming that the grabber 312 has rotated several times by action of the gear and shaft assembly 315. several loops 325 are formed in the suture material 305. The loops 325 become intertwined, and through the action of the tensioner 335, the suture material 305 is tensioned (e.g., pulled), for example, in the direction of the arrow in box 335 to form a knot in the suture material 305. The suture material may then be cut by blade 115 as shown in FIG. 1.

Figure 4:
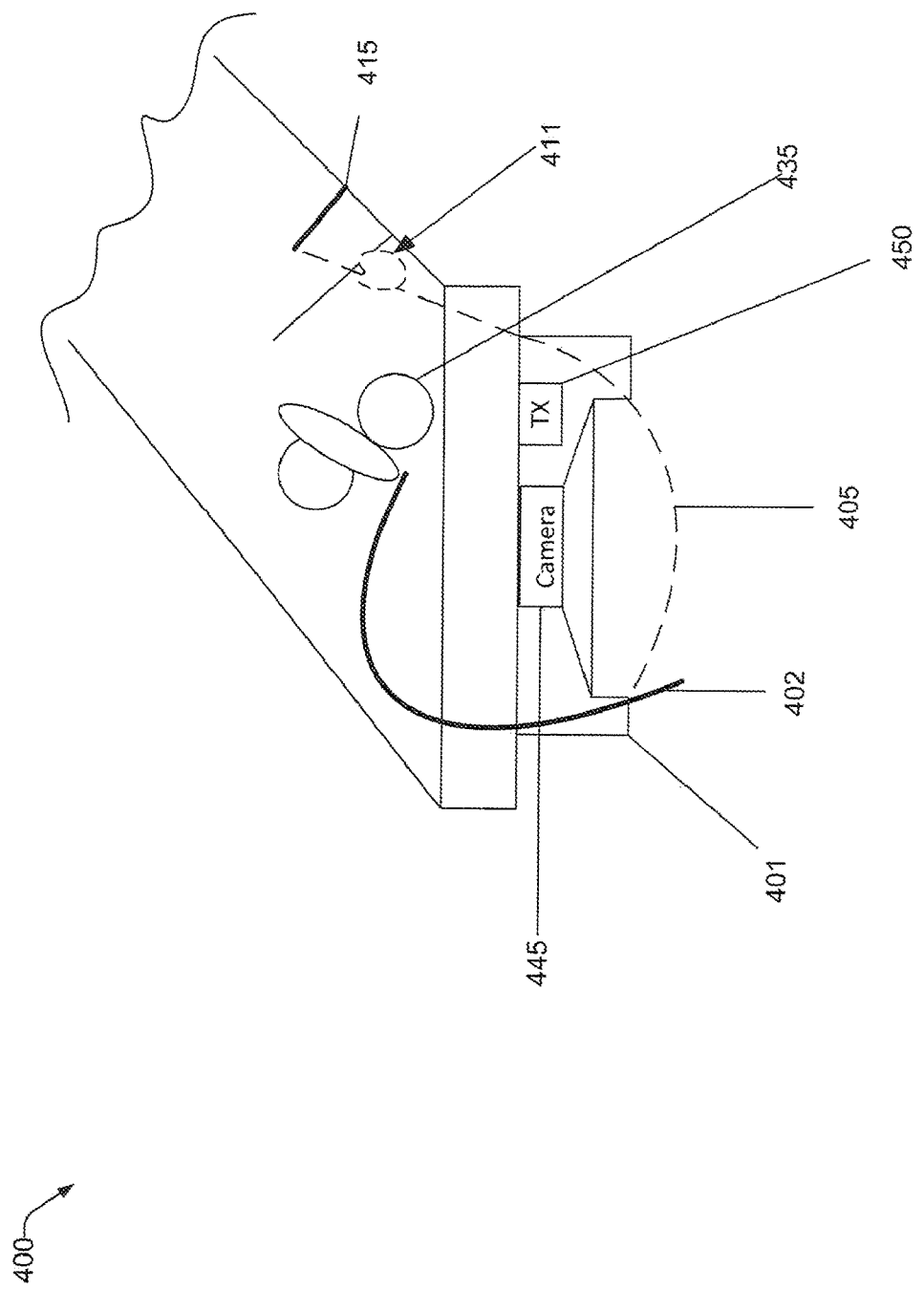
FIG. 4 illustrates a portion of the self-knotting suture device of FIG. 1 including a camera and a transmitter.

FIG. 4 illustrates a portion of the self-knotting suture device of FIG. 1 including a camera 445 and a transmitter 450. Also shown is a knot 411 made by the knotting mechanism, the cutter 415, gears 435 and needle 402. The base 401 has the camera 445, and the transmitter 450, which may be positioned as shown. Both components can be position in other positions than as shown in FIG. 4. The camera 455 can be any type of charged coupled device CCD, CMOS, etc. The transmitter 450 may be a wireless transmitter configured in a protocol such as WiFi or Bluetooth®. The transmitter 450 may transmit the image during the operation of the suture device to a smartphone, tablet, display, storage device, server, etc. Alternatively, the suture device 100 may have an embedded display 125 as shown in FIG. 1 that displays image received by the camera 445. The transmitter 450 may be configured for wired transmission to the embedded display 125 (shown in FIG. 1), or could be a wireless transmission. In addition, the transmitter 450 transmit an image to both the embedded display 125, and a wireless device. The wireless device may have a storage capacity to record the images so the stitching procedure can be reviewed by health practitioners, for example, for teaching and critique purposes.

CONCLUSION

The embodiments of the suture device of the present disclosure shown and described herein are not exhaustive in their teachings. The suture device as described above includes advantages in that it is efficient and easy to use, lowers puncture risk when suturing from pliers and knotting performed by hand using other components, and eliminates the need for pliers (e.g., needle nose pliers) and scissors. In a disposable version of the suture device, there is a cost savings of sterilization paper packets and sterilizing the medical equipment. In addition, the suture device enables a fast closure for field-dressing wounds that may occur in a combat environment or accident, traumatic injury, etc. The suture device is also scalable in size for use in different environments (e.g. robot, laparoscopic). The suture device can be constructed in mechanical and electro-mechanical versions, as discussed herein above. In a single use disposable version, a power source, including but not limited in any to a lithium battery can be part of the construction. A power port can be used to plug a power source to the device, for example, from a smartphone, tablet, battery, using any standard, including but not limited in any way to USB, micro USB, Apple® lightening, etc.

The descriptions of the various embodiments of the present teachings have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The components, operations, steps, features, objects, benefits, and advantages that have been discussed herein are merely illustrative. None of them, nor the discussions relating to them, are intended to limit the scope of protection. While various advantages have been discussed herein, it will be understood that not all embodiments necessarily include all advantages. Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

Numerous other embodiments are also contemplated. These include embodiments that have fewer, additional, and/or different components, steps, features, objects, benefits and advantages. These also include embodiments in which the components and/or steps are arranged and/or ordered differently. It is to be understood that optional components such as a camera and/or the positioning of the camera, and the presence of the display and/or its positioning, are provided for illustrative purposes and do not limit the scope of the appended claims. Such components can be included in some embodiments but not included in others.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any such actual relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

What is claimed is:

1. A self-knotting suture device, comprising:
a base configured for contact with a living tissue, wherein the base includes an opening for passage of a suture material;
a knotting mechanism including:
a finger configured to receive an end of the suture material; and
a grabber configured to be arranged substantially transverse to the suture material in a path to the finger, the grabber configured to rotate and twist the suture material into one or more intertwined loops;
a tensioner configured to adjust a tension of the suture material to form a knot of the intertwined loops; and
a blade mechanism configured to cut the suture material adjacent the finger.

2. The self-knotting suture device according to claim 1, further comprising a needle assembly configured to receive the suture material and pierce the living tissue, and
a slide trigger configured to be slid from a first position to a second position to move a position of the needle to form a stitch in the living tissue with the suture material.

3. The self-knotting suture device according to claim 2, wherein the slide trigger is further configured to be slid to a third position to actuate the knotting mechanism to tie a knot in the suture material.

4. The self-knotting suture device according to claim 3, wherein the slide trigger is further configured to be slid to a fourth position to cut the knotted suture material.

5. The self-knotting suture device according to claim 2, wherein the slide trigger manually moves the needle and actuates the knotting mechanism based on a position of the slide trigger.

6. The self-knotting suture device according to claim 2, further comprising a motor arranged to move the position of the needle and actuate the knotting mechanism based on a position of the slide trigger.

7. The self-knotting suture device according to claim 1, wherein the slide trigger further includes at least one button connected to a motor configured to move the needle, and at least a second button connected to the knotting mechanism.

8. The self-knotting suture device according to claim 1, wherein the slide trigger actuates the blade mechanism to cut the suture material when the slide trigger is moved to a cutting position.

9. The self-knotting suture device according to claim 1, wherein the grabber comprises a hook, and the knotting mechanism includes a gear and shaft assembly for rotating the hook.

10. The self-knotting suture device according to claim 1, wherein the blade mechanism comprises a knife and an actuator connected to the knife.

11. The self-knotting suture device according to claim 10, wherein the actuator includes a spring.

12. The self-knotting suture device according to claim 1, further comprising a housing in which the knotting mechanism and blade mechanism are arranged.

13. The self-knotting suture device according to claim 12, further comprising a handle attached to the housing.

14. The self-knotting suture device according to claim 13, further comprising grips attached to an exterior of the handle.

15. The self-knotting suture device according to claim 12, further comprising a camera arranged in the base, and a wireless transmitter.

16. The self-knotting suture device according to claim 15, further comprising a display arranged in the housing, the display is configured to display images received by the camera in the base.

17. A self-knotting suture device, comprising:
a base configured for contact with a living tissue, wherein the base includes an opening for passage of a suture material;
a tensioner configured to adjust a tension of the suture material;
a knotting means for twisting the suture material into one or more intertwined loops to form a knot of the intertwined loops; and
a blade mechanism configured to cut the suture material extending from the knot.

18. The self-knotting suture device according to claim 17, wherein the base is configured for contact with internal living tissue, and the device further comprising a camera arranged in the base, and a wireless transmitter configured to transmit the images from the camera.

19. The self-knotting suture device according to claim 17, wherein the knotting means is mechanically actuated.

20. The self-knotting suture device according to claim 17, wherein the knotting means is electrically actuated.

21. The self-knotting suture device according to claim 17, wherein the knotting means is actuated via a slide trigger.

* * * * *